United States Patent [19]

Breque et al.

[11] Patent Number: 4,504,683

[45] Date of Patent: Mar. 12, 1985

[54] PHOSPHOLES WITH FUNCTIONAL SUBSTITUENTS ON THE PHOSPHORUS AND PROCESS FOR THE PREPARATION OF PHOSPHOLES

[75] Inventors: Anne Breque, Mennecy; Georges Muller, Boutigny s/Essonne; Hubert Bonnard, Bretigny s/Orge; Francois Mathey; Philippe Savignac, both of Paris, all of France

[73] Assignees: Institut National de Recherche Chimique Appliquee (IRCHA); Centre National de la Recherche Scientifique, both of France

[21] Appl. No.: 265,312

[22] Filed: May 20, 1981

[30] Foreign Application Priority Data

May 28, 1980 [FR] France .................. 80 11818

[51] Int. Cl.³ .................................. C07F 9/50
[52] U.S. Cl. .................................. 568/12
[58] Field of Search .......................... 568/12

[56] References Cited

U.S. PATENT DOCUMENTS

| | | | |
|---|---|---|---|
| 2,663,736 | 12/1953 | McCormack | 568/12 |
| 2,663,737 | 12/1953 | McCormack | 568/12 |
| 2,663,738 | 12/1953 | McCormack | 568/12 |
| 2,853,518 | 9/1958 | Balon | 568/12 |
| 3,032,591 | 5/1962 | Henderson et al. | 568/12 |
| 3,069,246 | 12/1962 | Loper et al. | 568/12 X |
| 3,086,053 | 4/1963 | Wagner | 568/12 |
| 3,338,941 | 8/1967 | Braye | 568/12 X |

OTHER PUBLICATIONS

Mathey et al., Canadian J. Chem. pp. 2402-2410 (1976).
Quin et al., Journal of Organic Chemistry vol. 38, No. 10, pp. 1858-1866 (1973).
Chemical Abstracts, vol. 90, 38502m (1979).
Chemical Abstracts, vol. 86, 16742e (1977).

*Primary Examiner*—Helen M. S. Sneed
*Attorney, Agent, or Firm*—Karl W. Flocks; Sheridan Neimark

[57] ABSTRACT

The phospholes and P-functional phospholes correspond to the general formula:

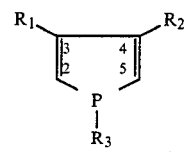

in which: $R_1$ and $R_2$ are identical or different and represent hydrogen or a lower alkyl group of $C_1$ to $C_4$ such as a methyl group, and $R_3$ represents an aryl group (such as $-C_6H_5$) or a substituted aryl group (such as $-CH_2C_6H_5$) or an alkyl group (such as $-CH_3$, $-C_2H_5$, $-C_3H_7$ to $C_{12}H_{25}$) or a $-(CH_2)_nZ$ group where Z denotes a function of the —COO-alkyl type (such as $-COOC_2H_5$), —CH, —CO-aryl (such as $-COC_6H_5$), —CO-alkyl (such as $-COCH_3$) or —OH and $n \geq 1$. At least one alkyl- or arylhalogeno phosphine is reacted with a butadiene whose carbons in the 2 and/or 3 positions carry possibly a lower alkyl substituent, the cyclic adduct resulting from this reaction is then subjected to the action of a tertiary amine selected from among those having a pKa comprised between 5 and 11, then the product obtained is functionalized if the corresponding P-functional product is desired. Some of the phospholes thus produced are novel, particularly those of the above formula wherein $R_3 = -(CH_2)_nZ$ such as above defined with $n \neq 2$ for Z=CN.

10 Claims, No Drawings

PHOSPHOLES WITH FUNCTIONAL SUBSTITUENTS ON THE PHOSPHORUS AND PROCESS FOR THE PREPARATION OF PHOSPHOLES

BACKGROUND OF THE INVENTION

The present invention relates to the production of phospholes, and to phospholes comprising functional substituents on the phosphorus, these compounds corresponding to the general formula:

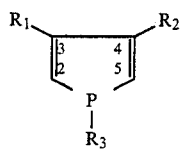

in which:
$R_1$ and $R_2$ are identical or different and represent hydrogen or a lower alkyl group of $C_1$ to $C_4$ such as a methyl group, and
$R_3$ represents a group $-C_6H_5$, $-CH_2-C_6H_5$, $-CH_3$, $-C_2H_5$, $-C_3H_7$ to $C_{12}C_{25}$ or $-(CH_2)_nZ$ where Z denotes a function $-COO$-alkyl (such as $-COOC_2H_5$), $-CN$, $-CO$-aryl (such as ($-CO-C_6H_5$), $-CO$-alkyl (such as $-CO-CH_3$), or $-OH$ and $n \geq 1$.

Among these compounds, those corresponding to the above formula, in which $R_1$ and $R_2$ have the given meaning and $R_3$ represents $-(CH_2)_nZ$ where Z denotes a $-COO$-alkyl (such as $-COOC_2H_5$), $-CN$, $-CO$-aryl (such as $-CO-C_6H_5$), $-CO$-alkyl (such as $-CO-CH_3$) or OH and $n \geq 1$ with $n \neq 2$ for $Z=CN$, constitute novel industrial products.

The preparation of phospholes is already known by means of the reaction of a dihalogenalkyl or aryl-phosphine with a butadiene whose carbons in the 2 and/or 3 position possibly bear a methyl substituent to obtain a cyclic addition product (called below "cyclic adduct") (see U.S. Pat. Nos. 2,663,736 and 2,663,737 and Chem Abstracts, 497601a–7602c (1955)), then subjecting said adduct to the action of diazobicyclo-undecene (DBU) (see: F. MATHEY and al. Org. Magn. Resonance, 4, 171 (1972) and L. D. QUIN and al. J. Org. Chem., 38, 1858 (1973).

Now, this process of preparation is not devoid of drawbacks resulting from the use of DBU which is an expensive product (which is prepared in three steps and which is difficult to purify and to dry), from the appearance of side-reactions competing with the main reaction, from the practical difficulties of processing the adducts due to the solvent nature of the DBU and finally from the very moderate yields and from the greater or lesser purity of the products obtained.

It is a particular object of the present invention to overcome these drawbacks and more especially to provide phospholes obtainable with good yields and of high purity. The attaining of this objective is all the more advantageous if the needs of industry for these necessitate large amounts having the required purity and at low price.

In other respects, at the present time, very few simple P-functional phospholes have been prepared.

Now, it is also an object of the invention to provide novel phospholes and a process enabling them to be obtaind.

GENERAL DESCRIPTION OF THE INVENTION

The process according to the invention is essentially characterised by the fact that at least one alkyl- or aryl-halogeno-phosphine is reacted with a butadiene of which the carbons in the 2 and/or 3 positions possibly bear a lower alkyl substituent, then the cyclic adduct resulting from this reaction is subjected to the action of a tertiary amine selected preferably from among those having a pKa comprised between 5 and 11, then the product obtained is functionalized if the corresponding P-functional product is desired.

According to an advantageous embodiment, a mixture of two different halogeno-phosphines is reacted.

In the case where use is made (as arylhalogeno-phosphines) of phenylhalogeno-phosphines, the latter are advantageously selected from among phenyldichloro- and phenyldibromophosphines. When recourse is had to mixtures of two different phenylhalogeno-phosphines, the latter are used in equal proportions.

The amines advantageously used according to the invention and leading to unexpectedly good yields are selected from among: picolines, triethylamine, tetramethylene diamine, 2-ethyl-pyridine, methyl-morpholine, N-methyl-imidazole, pyridine, N-methyl-pyrrolidine, 4-ethyl-pyridine.

In a suitable embodiment, the reaction between the one or more halogeno-phosphines and a butadiene is carried out at a temperature approaching 0° C. in a closed vessel, under an inert atmosphere, and in the absence of any organic solvent; and the reaction of the resulting product with the selected amine is conducted in a mixture of inert organic diluents of which at least one is a saturated hydrocarbon.

The P-functional phospholés are obtained by subjecting the phospholes resulting from the above reactions to a reaction consisting of opening the P-aryl or P-alkyl bond and obtaining an organo-metallic compound, then of causing the latter to react with a compound $X-(CH_2)_nZ$ where X is a halogen and Z has the previously given meaning.

According to a particular embodiment, the opening of the P-aryl or P-alkyl bond is effected by the action of an alkali metal (such as Li, Na, K) in the form of solubilised anion radicals (such as sodium naphthalene, lithium naphthalene, potassium naphthalene), in a polar basic ether solvent such as tetrahydrofurane (THF), dioxane, diglycine, dimethoxyethane, at a temperature preferably comprised between 0° and 25° C.

According to another embodiment, the opening of the P-phenyl bond is carried out by means of a non-solubilised alkali metal (such as Li, Na, K) in the presence of a polar basic ether solvent selected from among those mentioned above, at a temperature comprised between 10° and 40° C.

Advantageously, the phospholyl-alkali metal is converted into a metallic compound such as Mg, Zn, Cd by the action of the corresponding metal halogenide $MX_2$ where M=metal and X=Cl, Br, I.

The following reaction diagrams illustrate the various reactions; in these diagrams: Ma=alkali metal; M=Mg, Zn or Cd and X=Cl, Br, or I.

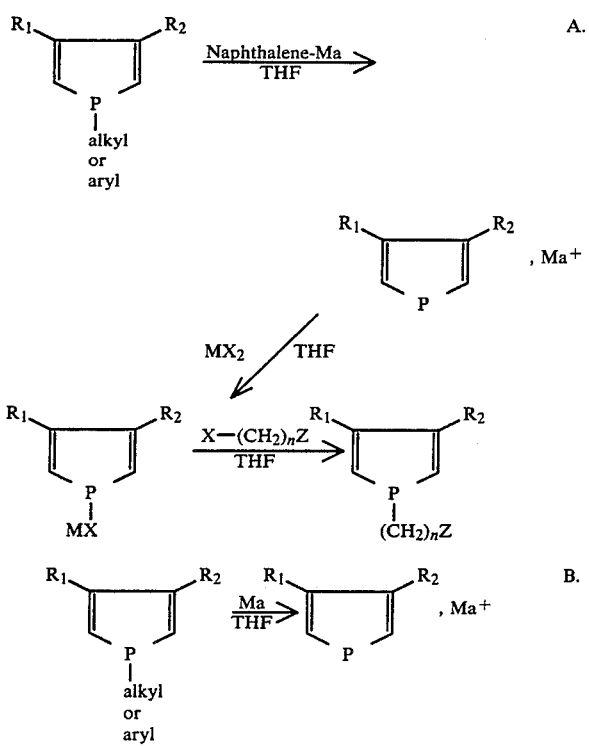

then as in diagram A, reaction with $MX_2$ then $X-(CH_2)_nZ$.

In these diagrams, the symbols $R_1$, $R_2$, X and n have the previously given meaning.

DESCRIPTION OF PARTICULAR EMBODIMENTS

The following examples are given by way of illustration of the invention and are to be considered as in no way limiting.

EXAMPLE 1

Preparation of the adduct (a)

In a 3-neck reactor of 1,000 cm³ previously purged with nitrogen, 53.6 g of phenyldibromo-phosphine (0.2 mole) and 35.8 g of phenyldichloro-phosphine (0.2 mole) dissolved in 10 cm³ of dry methylene chloride were introduced and then, thirty minutes later, 34.5 g of 2,3-dimethyl-butadiene (0.4 mole+5%) were added.

The mixture was left to stand protected from light.

A solid hygroscopic product resulted.

(b)

Procedure was as under (a) but only using phenyldibromo-phosphine.

(c)

Procedure was as under (a) but only using phenyldichloro-phosphine and two equivalents of 2,3-dimethyl-butadiene.

(d)

Preparation of 1-phenyl 3,4-dimethyl phosphole

The reactor described under (a) is provided with a cooler, connected to a vibro-mixer with an isobaric vessel and then placed in a nitrogen atmosphere. 400 cm³ of hexane and 300 cm³ of dry and degasified methylene chloride was added; the adduct was broken into several fragments. With stirring, 82 g of alpha-picoline (0.8 mole+10%) dissolved in 100 cm³ of methylene chloride was introduced drop by drop keeping the temperature at 20° C. Stirring was maintained until the adduct disappeared; a clear yellow upper phase and an orange brown lower phase resulted. An aqueous solution of 3N hydrochloric acid was introduced until a test showed acidity to pH paper (about 60 cm³). The organic solution was decanted under a nitrogen atmosphere and washed with water (60 cm³), then with a saturated solution of potassium carbonate (2×60 cm³) until a test showed neutrality to pH paper; it was then dried over sodium sulfate and concentrated.

66.8 g of pure product was checked by NMR of the proton and of the phosphorus; it can be distilled under a good vacuum and under an inert atmosphere; b.p./0.1=89°-91° C. Overall yield: 83.5%.

EXAMPLES 2 TO 16

By treating as under (d) of Example 1, the adducts obtained as described under (a), (b) and (c) according to the nature of the amine used, 1-phenyl 3,4-dimethyl phosphole was prepared with the yields reported in the table below.

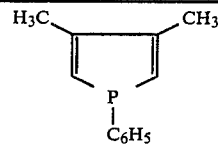

| Tertiary amine | Adduct preparation | Yield % |
|---|---|---|
| α-picoline | 1b | 83 |
| γ-picoline | 1b | 79 |
| Triethylamine | 1b | 66 |
| Tetramethylenediamine (TMEDA) | 1b | 78 |
| 2-ethyl-pyridine | 1b | 69 |
| Methyl-morpholine | 1b | 76 |
| N—methylimidazole | 1b | 73.5 |
| Pyridine | 1b | 74.5 |
| α-picoline | 1a | 72 |
| N—methyl pyrrolidine | 1b | 78 |
| TMEDA | 1a | 57 |
| α-picoline | 1c | 83 |

EXAMPLE 17

(a)

Into a 3-neck reactor of 1,000 cm³, previously purged with nitrogen, were placed 22.8 g of phenyldibromo-phosphine (0.085 mole) and 15.2 g of phenyldichloro-phosphine (0.085 mole) dissolved in 10 cm³ of dry methylene chloride, then, thirty minutes later, 12 g of isoprene (0.17 mole+5%) were added.

The mixture was left to stand protected from light; the product obtained was a hygroscopic solid.

(b)

Preparation identical with the preceding one but only using phenyldibromo-phosphine.

(c) 1-phenyl 3-methyl phosphole

The reactor was provided with a cooler, with a stirrer coupled to a vibro-mixer, an isobaric vessel and then placed under a nitrogen atmosphere. 200 cm³ of dry hexane and 100 cm³ of dry methylene chloride were introduced; the adduct prepared as under (a) was broken into several fragments. With stirring, 32 g of N-methyl pyrrolidine (0.34 mole+10%) dissolved in 100 cm³ of methylene chloride was introduced drop by drop. Stirring was kept up until the disappearance of the adduct. After having treated it as under (d) of Example 1, 23 g of crude product was obtained which was distilled. b.p./0.1=78°–80° C. Yield 60%.

EXAMPLES 18 TO 21

By treating as under (c) of Example 17 the adducts described as under (a) and (b) according to the nature of the tertiary amine, 1-phenyl 3-methyl phosphole was prepared with the following yields:

| Tertiary amine | Adduct preparation | Yield (%) |
|---|---|---|
| N—methyl pyrrolidine | 17b | 72 |
| γ-picoline | 17b | 50 |
| α-picoline | 17b | 40 |
| N—methyl imidazole | 17b | 22 |

EXAMPLE 22

(a)

Into a closed reactor of 1,000 cm³ adapted to withstand a pressure of 5 bars, were placed 80.4 g of phenyldibromophosphine (0.3 mole) and 30 cm³ of butadiene (0.3 mole+5%). The mixture was left to stand protected from light; the product obtained after depressurization of the reactor was a hygroscopic product.

(b) 1-phenyl phosphole

The reactor was provided with a cooler, a stirrer coupled to a vibromixer, and an isobaric vessel and then placed under a nitrogen atmosphere. 250 cm³ of dry hexane and 125 cm³ of methylene chloride were introduced; the adduct prepared as under (a) was broken into several fragments. After stirring, 61.5 g of alpha-picoline (0.6 mole+10%) dissolved in 125 cm³ of methylene chloride was introduced drop by drop. Stirring was kept up until disappearance of the adduct and it was treated as under (d) of Example 1. 32 g of crude product was obtained which was distilled. b.p./0.1=60°–65° C. Yield: 54%.

EXAMPLE 23

By proceding as under (b) of Example 22, with the treatment of the adduct obtained as under (a), 1-phenyl phosphole is prepared with a yield of 50% using N-methyl-pyrrolidine.

The following examples illustrate the preparation of P-functional phospholes according to the invention of which the characteristics have been easily determined in sulfide forms (see table below).

The NMR spectra have been recorded at 60 MHz on a Perkin-Elmer R24A for the proton at 36.447 MHz on a Bruker WP90 for the phosphorus. The I.R. spectra were recorded on a Perkin-Elmer 297 and 457, the mass spectra on an AEI MS-30 apparatus at 70 eV. All the reactions were conducted under argon with freshly distilled THF.

Method A—Sodium naphthalene-MgBr₂

In a well dried Erlenmeyer flask 6 g of naphthalene (0.047 mole) were dissolved in 100 cm³ of THF. 1 g of sodium (0.043 at-g) cut into small pieces was added. When all the sodium had reacted (about 1 hour), 4 cm³ of 1-phenyl-3,4-dimethyl phosphole (0.0213 mole) were added. The mixture was left to react for 5 hours at room temperature. Then 4 g of anhydrous $MgBr_2$ (0.0218 mole) was added and it was left to react further for 1 hour. It was transferred under argon into a dropping funnel and was added, drop by drop, to a solution of 0.025 mole of X—$(CH_2)_n$Z in 50 cm³ of THF. It was subjected to stirring over night. The next day, 1 g of flowers of sulfur (0.03 at-g) was added, and it was heated for 2 hours on an oil bath at 70° C. It was allowed to cool down, hydrolysed, neutralized if necessary with dilute HCl, the THF driven off, the residue extracted with methylene chloride, dried over $Na_2SO_4$ and evaporated to dryness. The essential part of the naphthalene was removed by sublimation at 40° C. under 1 torr. The residue was chromatographed on silica gel passing a sieve with meshes of 0.210 to 0.062 mm.

Method B—Opening the bond with an alkali metal such as Li 0.15 g of lithium (0.09216 at-g) in granules were suspended in 100 cm³ of THF. 2 cm³ of 1-phenyl-3,4-dimethylphosphole (0.01 mole) was added and it was left to react at 25° C. for 4 to 5 hours. A check was made to see if the opening of the bond was complete on silicagel plate ($Et_2O$ 50, Hexane 50). There was then added, either 2 g of anhydrous $MgBr_2$ (0.011 mole) or 2 g of anhydrous $CdCl_2$ (0.01 mole) and it was left with stirring for 1 hour at room temperature. Then the procedure was as for method A.

Product No. 60

Reagent: $BrCH_2COEt$

Eluent: Hexane 50/$Et_2O$ 50
Elementary anaylsis: $C_{10}H_{15}O_2PS$

|  | C (%) | H (%) |
|---|---|---|
| Calculated: | 52.16 | 6.57 |
| Found: | 51.92 | 6.50 |

Mass spectrum: m/e 230 (M, 32%): 143 (M—$CH_2COOEt$, 100%)

Product No. 80.

Reagent $BrCH_2CH_2CN$
Eluent: Hexane 40, AcOEt 60
Elementary analysis: $C_9H_{12}NPS$

|  | C (%) | H (%) | N (%) |
|---|---|---|---|
| Calculated: | 54.80 | 6.13 | 7.10 |
| Found: | 55.06 | 6.07 | 6.91 |

Mass spectrum: m/e 197 (M, 44%); 143 (M—$CH_2CH_2CN$, 100%)

Product No. 90.

Reagent: $BrCH_2C\ C_6H_5$

Eluent: Hexane 50 $Et_2O$ 50
Elementary analysis: $C_{14}H_{15}OPS$

|  | C (%) | H (%) |
|---|---|---|
| Calculated: | 64.10 | 5.76 |
| Found: | 64.22 | 5.74 |

Mass spectrum: m/e 262 (M, 26%); 143 (M—$CH_2COPh$, 100%)

Product No. 100.

-continued

Reageant: ClCH₂C CH₃
             ‖
             O

Eluent: Hexane 30 Et₂O 70
Elementary anlysis: C₉H₁₃OPS

|  | C (%) | H (%) |
|---|---|---|
| Calculated: | 53.98 | 6.54 |
| Found: | 54.80 | 6.46 |

Mass spectrum: m/e 200 (M, 45%); 143 (M—CH₂COMe, 100%)

Product No. 110.

Reageant: CH₂————CH₂.
           \    /
            O

In this particulae case, the reagent solution was poured into the magnesium or cadmium solution.
Eluent: AcOEt
Elementary anaylsis: C₉H₁₃OPS

|  | C (%) | H (%) |
|---|---|---|
| Caluculated: | 51.05 | 6.96 |
| Found: | 50.78 | 6.87 |

Mass spectrum: m/e (M, 46%); 144 (M—CH₂CH₂O, 100%).

stirred for 5 hours in all between 25° and 30° C. There was then added 4 g of anhydrous magnesium bromide and stirring was continued for 1 hour (partial decoloration). After removal of the excess unconverted lithium, the solution thus obtained was transferred, protected from moisture and air, into a dropping funnel mounted on a reactor of 500 cm³ containing 4 g of chloracetonitrile in 50 cm³ of anhydrous THF. The magnesium solution was added drop by drop into the nitrile with stirring. It was allowed to stand with stirring overnight at ordinary temperature. After 18 hours, it was hydrolysed with 50 cm³ of distilled water, the THF was evaporated and the phosphole extracted from the residual aqueous with hexane. The solution was dried over Na₂SO₄. After filtration and evaporation of the hexane, there was thus obtained 1.14 g of phosphole in the form of a colorless crystalline solid (yield: 35%).

Reaction diagram

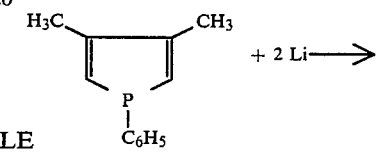 + 2 Li⟶

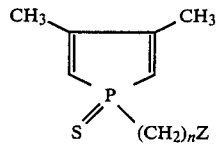

TABLE
Properties of the sulfides of P—functional phospholes

|  |  | Yield % |  |  | M.P. °C. | δ³¹P (CDCl₃) | I.R. | NMR of the Proton Ring |  |  | (CDCl₃) (CH₂)ₙZ |
|---|---|---|---|---|---|---|---|---|---|---|---|
| P(CH₂)ₙZ | N* | A | B | C | Kofler | (H₃PO₄) | (KBr) | CH₃ | CH(J_{H-P}) | PCH₂(j_{H-P}) | Z |
| PCH₂COEt<br>‖<br>O | 60 | 35 |  |  | 89 | 41.2 | ν_{CO}: 1728 cm⁻¹<br>ν_{PS}: 648 cm⁻¹ | 2.13 | 6.1 (31) | 3.2 (14) | CH₃: 1.37<br>CH₂: 4.23 J: 7Hz |
| PCH₂CH₂CN | 80 | 76 | 65 | 70 | 95–6 | 46.5 | ν_{CN}: 2245 cm⁻¹<br>ν_{PS}: 635 cm⁻¹ | 2.15 | 6.03 (31) |  | PCH₂CH₂: complex solid 2.2–3.0 |
| PCH₂C C₆H₅<br>‖<br>O | 90 | 22 |  | 18 | 131 | 40.7 | ν_{CO}: 1670 cm⁻¹<br>ν_{PS}: 632 cm⁻¹ | 2.1 | 6.05 (31) | 3.9 (15) | C₆H₅: 7.25–7.95 |
| PCH₂C CH₃<br>‖<br>O | 100 | 45 | 33 | 45 | 122 | 38.8 | ν_{CO}: 1710 cm⁻¹<br>ν_{PS}: 635 cm⁻¹ | 2.03 | 6.00 (15) | 3.17 (15) | CH₃: 2.3 |
| PCH₂CH₂OH | 110 | 45 | 12 | 18 | 118 | 45.5 | ν_{OH}: 3300 cm⁻¹<br>ν_{PS}: 615 cm⁻¹ | 2.03 | 5.93 (30) | 3.97 (20) | OH: 2.92<br>CH₂: 2.20(J_{H—H}: 5.5Hz) |

More particularly, the following example gives the preparation and the properties of 1-cyanomethyl-3,4-dimethyl phosphole of the formula:

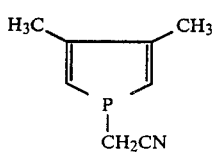

The whole operation was carried out under an inert gas (argon or nitrogen).

Into an Erlenmeyer flask provided with a magnetic stirrer were placed: 4 cm³ of 1-phenyl-3,4-dimethyl phosphole and 0.3 g of lithium in granules in 200 cm³ of anhydrous THF (tetrahydrofurane). The solution, colorless at the beginning changed to deep red. It was

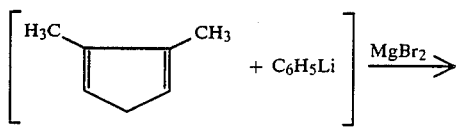

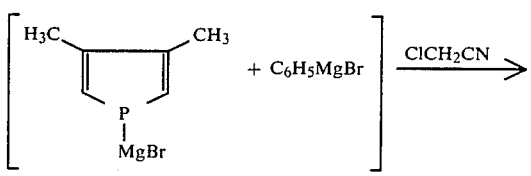

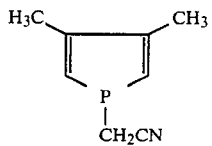

Properties of 1-cyanomethyl-3,4-dimethyl phosphole

NMR $^1$H (CDCl$_3$, TMS internal): δ2.07 (d, $^4$J(H-P) 3 Hz, 6H, CH$_3$); 2.63 (d, $^2$J(H-P) 5 Hz, 2H, CH$_2$CN); 6.12 (d, $^2$J(H-P) 40 Hz, 2H, CH-P) ppm NMR $^{31}$P (CHCl$_3$, H$_3$PO$_4$ external, +weak field) δ-23.4 ppm.

| Analysis: C$_3$H$_{10}$NP | | | |
|---|---|---|---|
| | C (%) | H (%) | N (%) |
| Calculated: | 63.57 | 6.62 | 9.27 |
| Found: | 63.9 | 6.8 | 9.0 |

It is self-evident that the description given of the present invention is purely by way of explanation and in no way limiting and that any useful modification could be introduced therein without departing from its scope as defined by the appended claims.

What is claimed is:

1. Process for preparing phospholes and P-functional phospholes corresponding to the general formula:

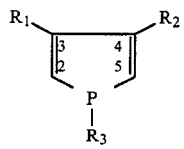

in which:

R$_1$ and R$_2$ are identical or different and represent hydrogen or a lower alkyl group of C$_1$ to C$_4$, and R$_3$ represents an aryl group; or a lower alkyl-substituted aryl group; or an alkyl group of C$_1$-C$_{12}$; or a —(CH$_2$)$_n$Z group where Z is a monovalent function of —COO-alkyl, —CN, —CO-aryl, —CO-alkyl or —OH and n≧1, which process comprises:

reacting at least one alkyl- or arylhalogeno phosphine with a butadiene whose carbons in at least one of the 2 and 3 positions carry possibly a lower alkyl substituent, then subjecting the resultant cyclic adduct to the action of a tertiary amine having a pKa between 5 and 11, and then optionally functionalizing the resultant product by splitting the P-alkyl or the P-aryl bond and by reacting a metal halide to obtain an organo metallic derivative, and then reacting the latter with a compound X—(CH$_2$)$_n$Z to provide the corresponding P-functional product.

2. Process according to claim 1, in which a mixture of two different halogeno phosphines is reacted.

3. Process according to claim 1, wherein said arylhalogeno-phosphines are phenylhalogeno phosphines selected from the group consisting of phenyldichloro and phenyldibromo-phosphines.

4. Process according to claim 1, wherein the amines are selected from the group consisting of: picolines, triethylamine, tetramethylethylene diamine, 2-ethylpyridine, methyl-morpholine, N-methylimidazole, pyridine, N-methyl-pyrrolidine, 4-ethylpyridine.

5. Process according to claim 1, wherein the reaction with butadiene is carried out at about 0° C. in a closed vessel under an inert atmosphere and in the absence of any organic solvent, and the reaction of the resulting product with the selected amine is conducted in a mixture of inert organic diluents of which at least one is a saturated hydrocarbon.

6. Process according to claim 1, wherein the splitting of the P-aryl or P-alkyl bond is carried out by the action of an alkali metal selected from the group consisting of lithium, sodium and potassium in the form of solubilized anion radicals selected from the group consisting of sodium naphthalene, lithium naphthalene, and potassium naphthalene in a polar basic ether solvent selected from the group consisting of tetrahydrofurane, dioxane, diglycine and dimethoxy-ethane, at a temperature comprised between 0° and 25° C.

7. Process according to claim 1, wherein the opening of the P-aryl or P-alkyl bond is carried out by the action of an alkali metal selected from the group consisting of lithium, sodium and potassium, non-solubilized, in the presence of a polar basic ether solvent selected from the group consisting of tetrahydrofurane, dioxane, diglycine and dimethoxy ethane, at a temperature between 10° and 40° C.

8. Process according to claim 1, wherein the metal halide is a MX$_2$ compound where M is Mg, Zn, or Cd, and X is Cl, Br or I.

9. A process according to claim 1 wherein R$_3$ is phenol, —CH$_2$C$_6$H$_5$, —CH$_3$, —C$_2$H$_5$, —C$_3$H$_7$ to C$_{12}$H$_{25}$, or a —(CH$_2$)$_n$Z group where Z is —COOC$_2$H$_5$, —CN, —COC$_6$H$_5$ or —COCH$_3$.

10. A process according to claim 2 wherein the mixture comprises equal proportions of phenylhalogenophosphines.

* * * * *